US011229532B2

(12) United States Patent
Smit et al.

(10) Patent No.: US 11,229,532 B2
(45) Date of Patent: Jan. 25, 2022

(54) PROSTHETIC HAND

(71) Applicant: Technische Universiteit Delft, Delft (NL)

(72) Inventors: Gerhardus Smit, Delft (NL); Bartjan Maat, Delft (NL)

(73) Assignee: TECHNISCHE UNIVERSITEIT DELFT, Delft (NL)

(*) Notice: Subject to any disclaimer, the term of this patent is extended or adjusted under 35 U.S.C. 154(b) by 324 days.

(21) Appl. No.: 16/014,896

(22) Filed: Jun. 21, 2018

(65) Prior Publication Data
US 2018/0296369 A1  Oct. 18, 2018

Related U.S. Application Data

(63) Continuation of application No. PCT/NL2016/050896, filed on Dec. 20, 2016.

(30) Foreign Application Priority Data

Dec. 21, 2015  (NL) ..................................... 2015998

(51) Int. Cl.
*A61F 2/58* (2006.01)
*A61F 2/68* (2006.01)
(Continued)

(52) U.S. Cl.
CPC .............. *A61F 2/586* (2013.01); *A61F 2/583* (2013.01); *A61F 2/585* (2013.01); *A61F 2/72* (2013.01);
(Continued)

(58) Field of Classification Search
CPC ............... A61F 2/54; A61F 2/58; A61F 2/583
(Continued)

(56) References Cited

U.S. PATENT DOCUMENTS 1,630,277 A  5/1927  Smith
2,549,792 A  4/1951  Fletcher
(Continued)

FOREIGN PATENT DOCUMENTS

GB  201654  8/1923
WO  2013/076683  5/2013
WO  2017/111582  6/2017

*Primary Examiner* — Marcia L Watkins
(74) *Attorney, Agent, or Firm* — Peacock Law P.C.; Justin Muehlmeyer

(57) ABSTRACT

Prosthetic hand (1) with a wrist (13) and provided with a hand palm (2) and fingers (4) attached to the hand palm (2), wherein the hand palm (2) and fingers (4) comprise bars (5) and joints (6) connecting the bars (5) forming a construction (7) supported by the wrist (13), wherein said bars (5) occupy a position with reference to each other de-pending on an external load applied to the construction (7), wherein a reaction force for said load applied to the construction (7) is provided by or through the wrist (13), and wherein the construction (7) has an unloaded position wherein the fingers (4) are stretched and a plurality of loaded positions corresponding to loads applied to an inner side of the hand (1) wherein the construction (7) is deflected from the unloaded position wherein the fingers (4) are stretched into a series of loaded positions in which the fingers (4) are flexed into increasingly bonded positions so as to eventually close the hand (1), and that said construction (7) is provided with a locking mechanism (9) to lock the construction (7) in one of the plurality of loaded positions.

9 Claims, 5 Drawing Sheets

(51) Int. Cl.
*A61F 2/72* (2006.01)
*B25J 15/00* (2006.01)
*B25J 15/10* (2006.01)
*A61F 2/50* (2006.01)

(52) U.S. Cl.
CPC ......... *B25J 15/0009* (2013.01); *B25J 15/103* (2013.01); *A61F 2002/5075* (2013.01); *A61F 2002/587* (2013.01); *A61F 2002/6818* (2013.01); *A61F 2002/6836* (2013.01); *A61F 2002/6854* (2013.01)

(58) Field of Classification Search
USPC .................................................... 623/57, 64
See application file for complete search history.

(56) References Cited

U.S. PATENT DOCUMENTS

| | | | | |
|---|---|---|---|---|
| 4,228,690 | A | * 10/1980 | Ring | ................... H01H 43/102 |
| | | | | 74/122 |
| 5,762,390 | A | 6/1998 | Gosselin et al. | |
| 2015/0230941 | A1 | * 8/2015 | Jury | ........................ A61F 2/586 |
| | | | | 623/64 |
| 2016/0367383 | A1 | * 12/2016 | Sensinger | ............... A61F 2/583 |

\* cited by examiner

PROSTHETIC HAND

CROSS-REFERENCE TO RELATED APPLICATIONS

This application is a continuation of International Application No. PCT/NL2016/050896, entitled "Prosthetic Hand", filed Dec. 20, 2016, which claims priority to and the benefit of Netherlands Patent Application No. 2015998, entitled "Prosthetic Hand", filed Dec. 21, 2015, and the specification and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND

The invention relates to a prosthetic hand with a hand palm and fingers attached to the hand palm, wherein the hand palm and fingers comprise bars and joints connecting the bars, which bars and joints provide at least one construction wherein said bars occupy a position with reference to each other depending on an external load applied to the construction.

Such a prosthetic hand is known from U.S. Pat. No. 5,762,390 disclosing a mechanical hand with three fingers, wherein each finger has three phalanges. This known mechanical hand can perform power grasps as well as pinch grasps and is designed for actuation by an external load by an actuating bar that is linked to the frame of the hand. Applying the load whilst an object is in the inner palm of the hand makes the fingers comply to the shape of the object. Releasing the object requires removing the external load.

U.S. Pat. No. 2,549,792 discloses a prosthetic hand with a wrist and provided with a hand palm, a thumb and fingers attached to the hand palm, wherein the hand palm and fingers comprise bars and joints connecting the bars forming a construction supported by the wrist, wherein inherently said bars occupy a position with reference to each other depending on a load applied to the construction. Accordingly, the construction has an unloaded position and a plurality of loaded positions corresponding to loads applied to the hand wherein the construction is deflected from the unloaded position. The construction is further provided with a locking mechanism to lock the construction in one of the plurality of loaded positions. The fingers and the hand palm cannot be flexed.

WO2013/076683 discloses an underactuated prosthetic hand in which a plurality of independent figure mechanisms are mechanically movable between open and closed positions by means of longitudinally movable elongate operating elements that are provided within the hand. In the closed position the fingers are flexed. The hand has no thumb.

U.S. Pat. No. 1,630,277 discloses an artificial hand comprising a palm plate with spiral spring fingers and thumb, flexible wires connected to each finger and thumb, flat springs projecting within each finger and thumb and operated by a movable plate through a pivoted ratchet sector.

GB 201,654 discloses an artificial hand in which a flexible wire and spiral spring are positioned in each finger and thumb, the use in each finger and thumb of a flat or rectangular spring passing through the spiral spring and connected to a movable plate or plates and means for operating said plate or plates so as to close and open the fingers and thumb.

BRIEF SUMMARY OF THE INVENTION

It is an object of the invention to provide a prosthetic hand with an autonomous grasping function, that is without requiring the application of additional measures to perform the grasping function.

It is another object of the invention to provide a prosthetic hand which better resembles a human hand particularly with reference to some of the faculties that a human hand has.

It is still another object of the invention to provide a prosthetic hand which is independent from any external power source, except for the human muscle power of a user of the prosthetic hand.

It is a further object of the invention that the prosthetic hand is capable to maintain a firm grasping or pinching of an object without external auxiliary means.

These and other objects of the invention as well as advantages that will become apparent from the following disclosure are promoted by a prosthetic hand having the features of one or more of the appended claims.

In a first aspect of the invention the prosthetic hand has a wrist and is provided with a hand palm and fingers attached to the hand palm, wherein the hand palm and fingers comprise bars and joints connecting the bars forming a construction supported by the wrist, wherein said bars occupy a position with reference to each other depending on an external load applied to the construction, wherein a reaction force for said load applied to the construction is provided by or through the wrist, and the construction has an unloaded position wherein the fingers are stretched and a plurality of loaded positions corresponding to loads applied to the thumb or to the inner palm of the hand wherein the construction is deflected from the unloaded position wherein the fingers are stretched into a series of loaded positions in which the fingers are flexed into increasingly bended positions so as to eventually close the hand, and that said construction is provided with a locking mechanism to lock the construction in one of the plurality of loaded positions. in this way it is possible to simply maintain a power grasp or a pinch grasp to an object or to apply a hook grasp and to maintain all these grasping functions without additional or auxiliary means.

It is remarked that the appended claims and the invention to which the claims relate also apply to a prosthetic hand comprising not only bars and joints, but also cables and/or pulleys. At locations where no bars are necessary, that is where only pulling forces occur, the bars can be replaced by cables. If such cables are applied at the inner palm of the hand it is even possible to extend a single cable beyond the location where otherwise a joint would be, and replace such joint by a pulley. A single cable and the pulley can then replace two bars and a joint.

The load applied to the hand can be applied to the thumb or to the inner palm of the hand and can be derived from a user moving the prosthetic hand towards the object to the grasped, wherein the users muscle power acts as the driving force that makes the hand close around the object.

The locking mechanism can for instance be embodied as a friction locking with cooperating friction surfaces that provide the locking function, or as a hydraulic locking with a closable valve. Also electronic locking means are possible. In a preferred and simple mechanical embodiment the locking mechanism comprises a ratchet mechanism having at least one gear with teeth and a pawl to lock the construction in one of the plurality of loaded positions.

Preferably the ratchet mechanism comprises two pawls that cooperate with the teeth of the at least one gear wherein the two pawls are arranged to intermittently engage said teeth to lock the construction in one of the plurality of loaded positions. in an alternative arrangement the ratchet mechanism comprises two adjacent gears with teeth and a pawl or pawls cooperating with said teeth for locking the construction, wherein the teeth of the adjacent gears are staggered such that the said gears provide a phase shift, for instance a 90° phase shift with respect to each other in relation to the pawl or pawls. This dual construction of two pawls intermittently engaging the teeth of the gear or gears, or alternatively the application of two gears with a predefined phase shift cooperating with one or two pawls doubles the number of possible lock positions wherein the prosthetic hand can grasp an object. in practice this means that the hand is well attuned to variations in the external dimensions of the object and can be used to grasp an object of any dimension provided that it is not larger than a maximum value.

Advantageously the prosthetic hand is provided with separate means for unlocking the ratchet mechanism so as to release the construction and to enable it to return to the unloaded position. A preferential embodiment of the prosthetic hand is construed with an extension that is provided on the pawl or pawls, and that the hand has a switch that is movable into a position that it will cooperate with the extension when a load is applied to the construction and in the inner palm of the hand or to the thumb to remove the pawl or pawls from the teeth of the gear or gears. By this construction it requires two actions to have the prosthetic hand return to the unloaded position; a first action to operate the switch so that it can cooperate with the extension on the pawl or pawls, and a second action to actually remove the pawl or pawls from the gear or gears so that the prosthetic hand can assume the unloaded position. The switch can be actuated directly or indirectly through electric actuation by the user's nerve system or by a muscle connection, or simply manually by the user's other hand.

Preferably at the side of the hand inner palm the construction is provided with bars that are slidable with reference to each other and wherein distant extremities of said bars are spring-loaded with a spring to provide the bars with a preferential position wherein said extremities are closest to each other. By providing this slidable arrangement of the bars it is possible for the prosthetic hand to receive higher loads that deflect the construction further away from its unloaded position than is the case without the sliding bar arrangement, so that the ratchet mechanism can adjust to this higher load and maintain it.

In another aspect of the invention the hand is provided with multiple fingers and a thumb, wherein the thumb is mounted on a bar of the construction at the back of the hand. This construction effectively enables that the prosthetic hand of the invention can perform pinch grasping.

In a suitable arrangement the hand has four fingers, each of the four fingers being embodied with a construction, wherein at least one of the fingers is independently movable with respect to the other fingers. This enables that the prosthetic hand can easily adjust to various shapes of the objects to be grasped. An appropriate way of implementing this independent movement is by arranging that a bar of said at least one finger is through an intermediate swivel bar mounted to a joint at its base.

The invention will hereinafter be further elucidated with reference to the drawing of an exemplary embodiment of an apparatus according to the invention that is not limiting as to the appended claims.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims (if any).

BRIEF DESCRIPTION OF THE SEVERAL VIEWS OF THE DRAWINGS

The accompanying drawings in the attachment, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawing.

Whenever in the figures the same reference numerals are applied, these numerals refer to the same parts.

DETAILED DESCRIPTION OF THE INVENTION

Figure 1:
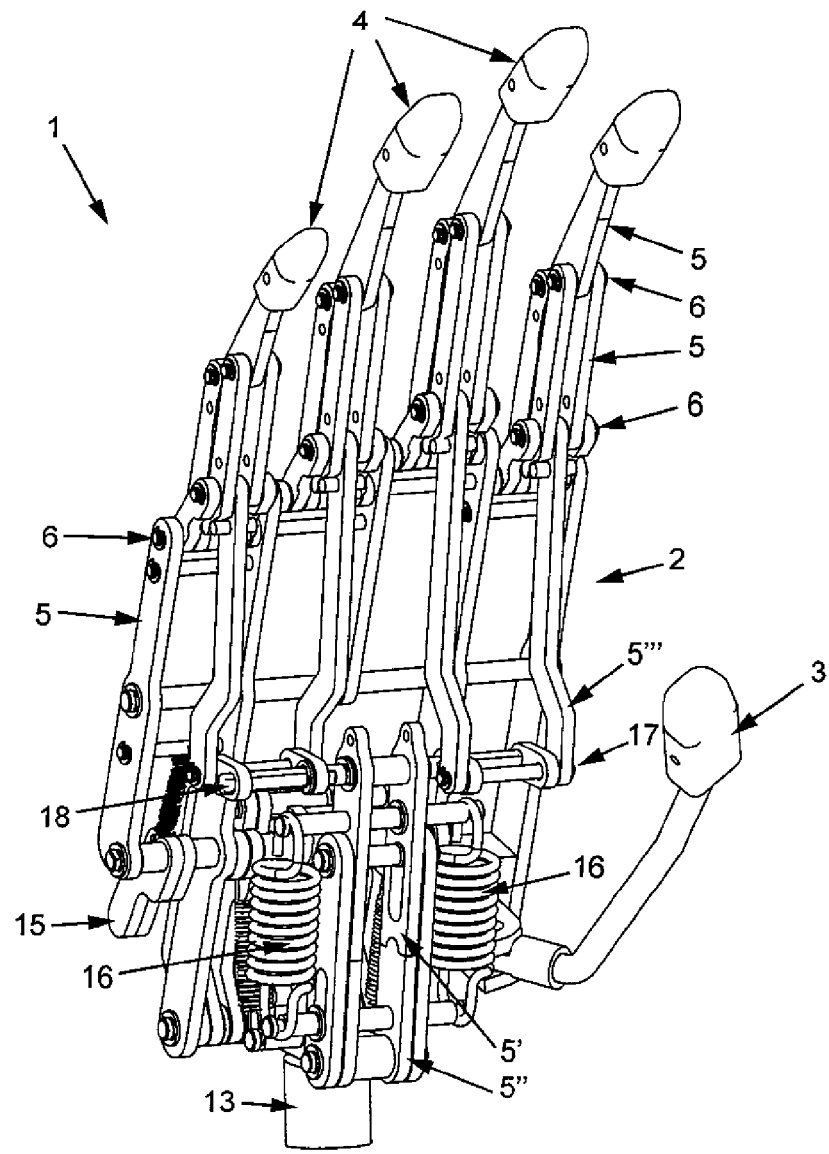
FIG. 1 shows a prosthetic hand according to the invention in an unloaded position.
Figure 2:
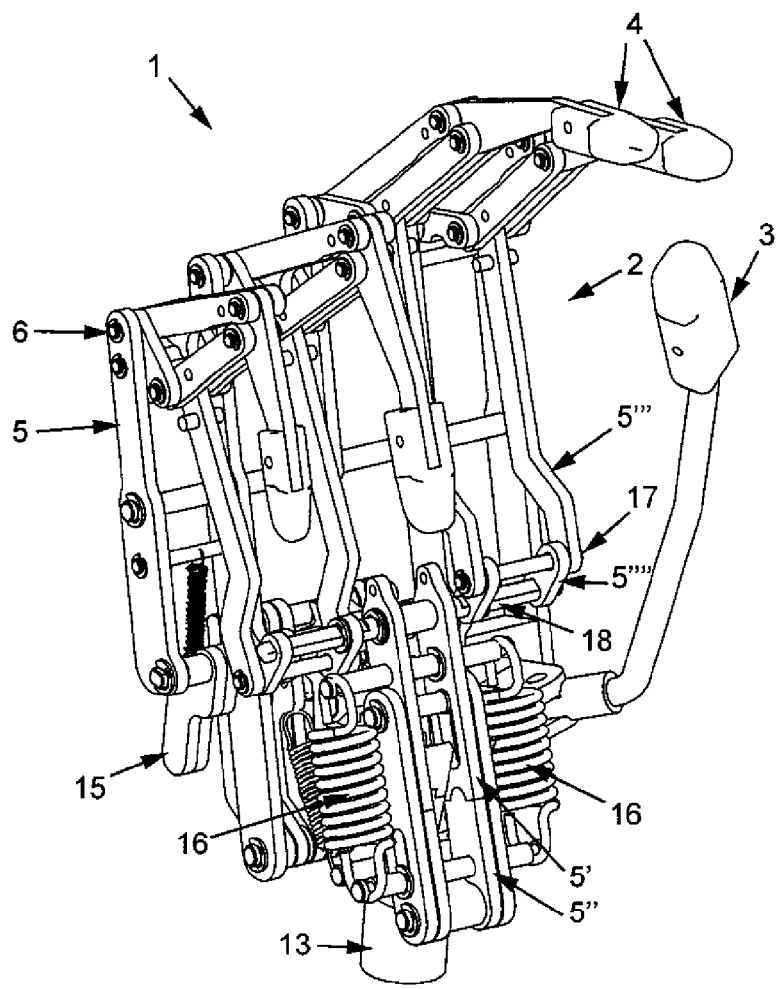
FIG. 2 shows the prosthetic hand of FIG. 1 in a pinch grasp position.
Figures 3A, 3B, 3C:
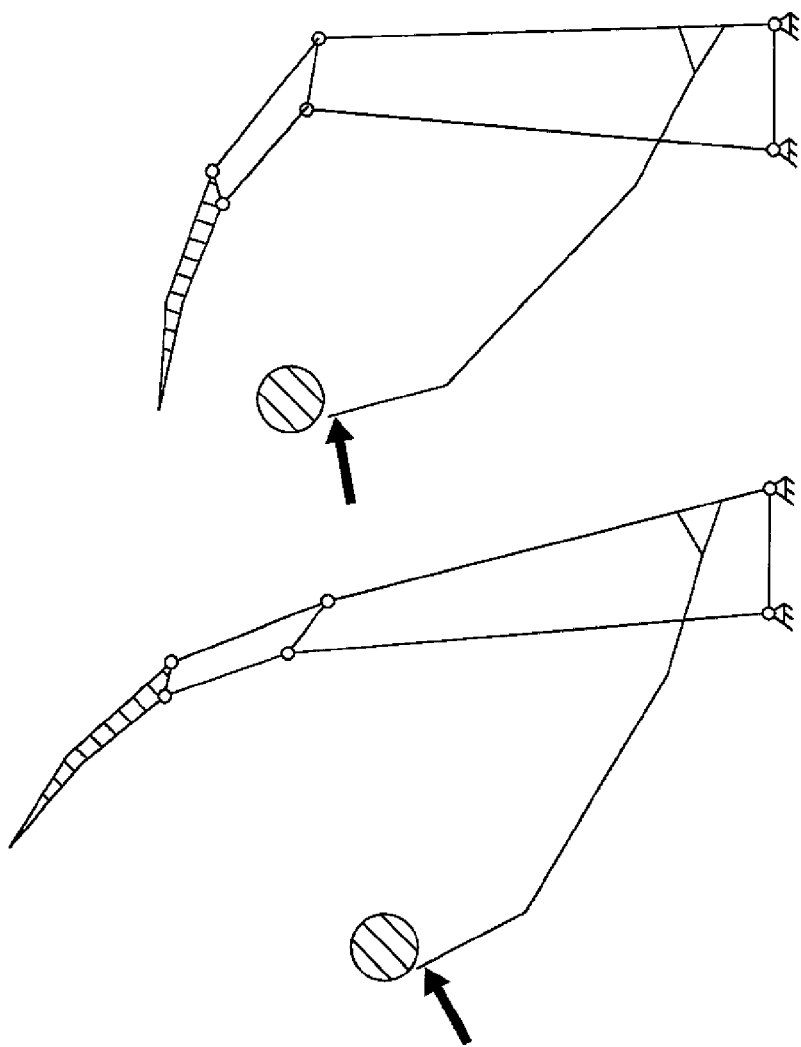
FIGS. 3A-C schematically show he prosthetic hand of the invention moving towards the pinch grasp position of FIG. 2.

FIG. 1 shows the prosthetic hand 1 of the invention which has a hand inner palm 2, and a thumb 3 and fingers 4 attached to the hand inner palm 2. The hand inner palm 2 and the fingers 4 comprise bars 5 and joints 6 connecting the bars 5. FIG. 3 provides a schematic drawing which more clearly shows that the bars 5 and joints 6 provide at least one construction 7. Otherwise FIG. 3 provides a sequential view at the pinching operation of the prosthetic hand 1 of the invention by a cooperation of the thumb 3 and the finger 4 by looking first at FIG. 3A and then looking at FIG. 3B and FIG. 3C. The pinching position of the prosthetic hand 1 of FIG. 3C is also shown in FIG. 2.

Turning now to the schematic representation of FIG. 5 it is shown that the bars 5 of the construction 7 occupy a position with reference to each other depending on an external load applied to the construction 7 at the location of the inner palm 2 of the hand, in this case by the object 8. The load of the hand could also be applied to the thumb 3.

Figure 5G:
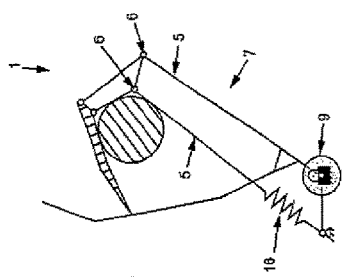
FIGS. 5A-G schematically show the prosthetic hand of the invention in a series of motions resulting into grasping a circular object.
Figure 5F:
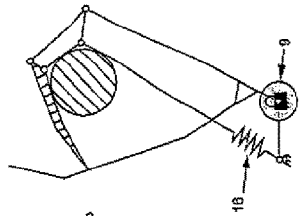
Figure 5E:
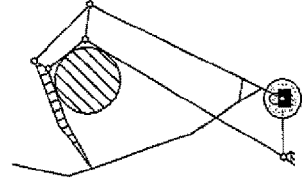
Figure 5D:
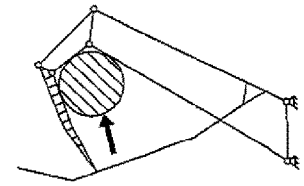
Figure 5C:
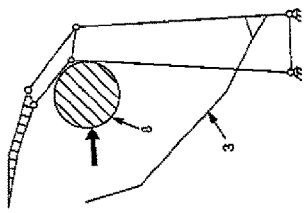
Figure 5B:
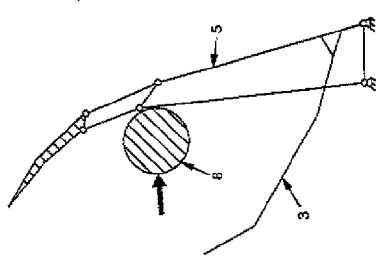
Figure 5A:
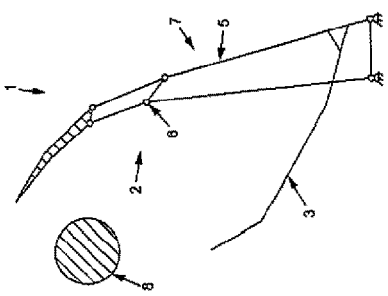

FIG. 5A corresponds to FIG. 1 and shows the prosthetic hand 1 wherein the construction 7 is in its unloaded position wherein the fingers 4 are stretched. Going from FIG. 5A to FIG. 5G the construction 7 travels through a plurality of loaded positions corresponding to loads applied by the object 8 into the inner palm 2 of the hand. Correspondingly the construction 7 is deflected from the unloaded position of FIG. 5A into eventually the position shown in FIG. 5G. Accordingly the hand 1 travels from the unloaded position wherein the fingers 4 are stretched into a series of loaded positions in which the fingers 4 are flexed into increasingly bended positions so as to eventually close the hand 1 as depicted in FIG. 5G.

According to a preferred embodiment of the invention the said construction 7 is provided with a ratchet mechanism 9 as symbolically indicated in FIGS. 5F and 5G to lock the construction 7 in one of the plurality of loaded positions as shown in FIGS. 5B-5G. The ratchet mechanism 9 acts as a locking mechanism for the construction 7. It is however also possible to apply other constructions for locking of the construction 7 in one of its loaded positions. The locking mechanism can for instance also be embodied as a friction locking with cooperating friction surfaces that provide the locking function, or as a hydraulic locking with a closable valve. Also electronic locking means are possible. It is also possible to apply another location for the locking mechanism than is shown in the figures, or to apply multiple locking mechanisms in line with the general meaning of drawings as not being restrictive for the protective scope of the claims.

Figure 4C:
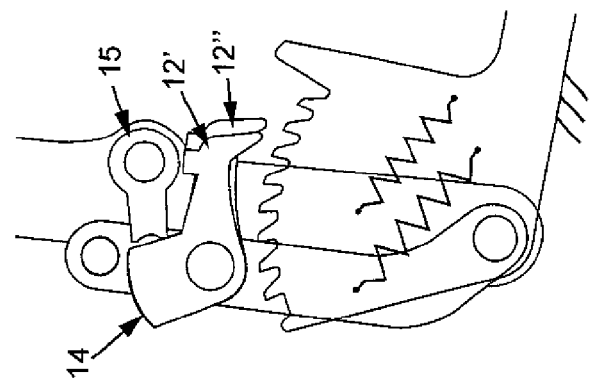
FIGS. 4A-4C show an embodiment of the ratchet mechanism forming part of the prosthetic hand of the invention.
Figure 4B:
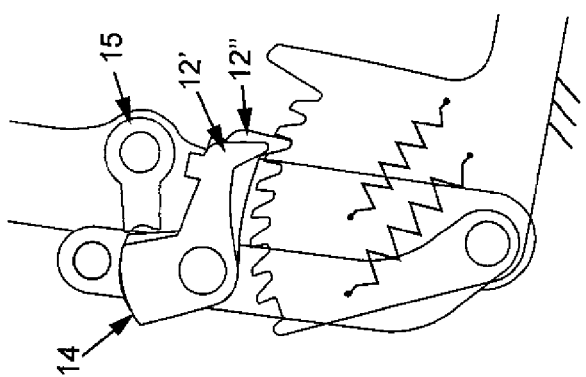
Figure 4A:
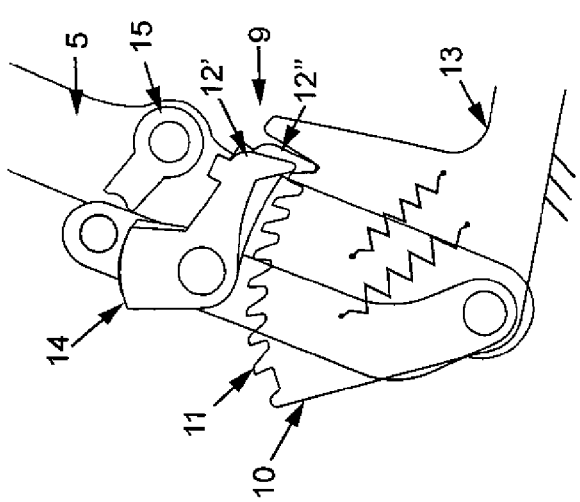

In FIGS. 4A-4C a detailed view is provided to the preferably applied ratchet mechanism 9 which is embodied with at least one gear 10 with teeth 11 that cooperate with at least one pawl 12', 12". The figure shows two pawls 12', 12" and the functionality of these two pawls will be explained hereinafter. The gear 10 is fixedly mounted on the base or wrist 13, which is also shown in FIG. 1. The at least one pawl 12', 12" is mounted on a bar 5 at the backside of the prosthetic hand 1. Consequently the inner palm 2 of the hand is located at the right-hand side of the ratchet mechanism shown in FIG. 4A. When a force to the left is applied to the bar 5, the pawl or pawls 12', 12" will travel along the teeth 11 of the gear 10 as shown in FIG. 4B. Accordingly the construction 7 moving through the series of loaded positions shown in FIG. 5 is arrested in its final position by one of the pawls 12', 12" becoming engaged with one of the teeth 11 at which it remains.

The reason to apply two pawls 12', 12" that cooperate with the teeth 11 of the gear 10 is that these two pawls 12', 12" can then be arranged to intermittently engage said teeth 11 of the gear 10 to lock the construction 7 in one of the plurality of loaded positions. By doing so a more accurate tuning is provided of the configuration of the construction 7 and the corresponding positions at which the pawls 12', 12" may be arrested by the teeth 11 of the gear 10.

In a not shown alternative embodiment the ratchet mechanism 9 comprises two adjacent gears with teeth and a pawl or pawls 12', 12" cooperating with said teeth for locking the construction 7, wherein the teeth of the adjacent gears are staggered such that the said gears provide a phase shift, for instance a 90° phase shift with respect to each other in relation to the pawl or pawls 12', 12". As will be clear from the foregoing a combination of two gears with one pawl or with two pawls is possible. All in all these various embodiments provide for a more accurate tuning of the positions at which the pawl or pawls 12', 12" may be arrested by the teeth of the gear or gears.

In FIGS. 4A-4C it is further shown that an extension 14 is provided on the pawl or pawls 12', 12". This extension 14 is used in the process of unlocking the ratchet mechanism 9 to release the construction 7 and enable it to return to the unloaded position of FIGS. 1, 3A and 5A. For that purpose the prosthetic hand 1 also has a switch 15 which can be brought in a position as shown in FIG. 4B so that it can cooperate with the extension 14 of the pawl or pawls 12', 12". This cooperation will then take place when after placement of the switch 15 in the proper position a load is applied to the construction 7 in the inner palm 2 of the hand which switch 15 will then remove the pawl or pawls 12', 12" from the teeth 11 of the gear 10 or gears, as depicted in FIG. 4C.

Turning back to FIGS. 1 and 2 it is shown that at the side of the hand inner palm 2 the construction 7 is provided with bars 5', 5" that are slidable with reference to each other and that distant extremities of said bars 5', 5" are spring-loaded by springs 16—as also schematically depicted in FIGS. 5F and 5G—to provide the bars 5', 5" with a preferential position of said extremities in which they are closest to each other. The sliding arrangement of the bars 5', 5" provide the prosthetic hand 1 of the invention with an increased range of deflected positions of the construction 7. In other words: the positions shown in FIGS. 5F and 5G are made possible by the sliding arrangement of the bars 5', 5".

FIGS. 1 and 2 further show that the prosthetic hand 1 that is provided with multiple fingers 4 and a thumb 3, wherein the thumb 3 is mounted on a bar of the construction 7 of one of the fingers, and wherein said bar is located at the back of the hand. Preferably the hand has four fingers as shown in FIGS. 1 and 2, wherein each of the four fingers 4 is embodied with a construction, and wherein at least one of the fingers is independently movable with respect to the other fingers. For that purpose it is preferable that a bar 5''' of said at least one finger is through an intermediate swivel bar 5'''' mounted to a joint 17 at its base 18.

Although the invention has been discussed in the foregoing with reference to an exemplary embodiment of the prosthetic hand of the invention, the invention is not restricted to this particular embodiment which can be varied in many ways without departing from the invention. The discussed exemplary embodiment shall therefore not be used to construe the appended claims strictly in accordance therewith. On the contrary the embodiment is merely intended to explain the wording of the appended claims without intent to limit the claims to this exemplary embodiment. The scope of protection of the invention shall therefore be construed in accordance with the appended claims only, wherein a possible ambiguity in the wording of the claims shall be resolved using this exemplary embodiment. The entire disclosures of all references, applications, patents, and publications cited above and/or in the attachments, and of the corresponding application(s), are hereby incorporated by reference.

What is claimed is:

1. A prosthetic hand comprising:
   a wrist;
   a hand palm comprising an inner side and a back side;
   a thumb; and
   wherein the hand palm comprises at least one construction rotatably supported by the wrist, the construction comprising a finger, bars and joints connecting the bars,
   wherein the bars of the finger occupy a position with reference to each other and a deflected position with reference to the wrist depending on, and in a direction of an external load applied to the construction, wherein a reaction force for the load applied to the construction is provided by or through the wrist, wherein the construction has an unloaded position wherein the finger is stretched and a plurality of loaded positions corresponding to loads applied to the thumb or to the inner side of the hand palm wherein the construction is deflected from the unloaded position wherein the finger is stretched into the plurality of loaded positions in which the finger is deflected with reference to the wrist and flexed into increasingly bended positions so as to eventually close the prosthetic hand, and wherein the construction further comprises a locking mechanism to lock the construction in one of the plurality of loaded positions.

2. The prosthetic hand according to claim 1 wherein the locking mechanism comprises a ratchet mechanism comprising a gear with teeth and a pawl to lock the construction in one of the plurality of loaded positions.

3. The prosthetic hand according to claim 2, wherein the ratchet mechanism comprises two pawls that cooperate with the teeth of the gear wherein the two pawls are arranged to intermittently engage the teeth to lock the construction in one of the plurality of loaded positions.

4. The prosthetic hand according to claim 2 wherein the construction is configured such that unlocking the ratchet mechanism releases the construction to enable it to return to the unloaded position.

5. The prosthetic hand according to claim 2 further comprising an extension disposed on the pawl, and the hand further comprising a switch that is movable into a position wherein it will cooperate with the extension when a load is applied to the construction to remove the pawl from the teeth of the gear.

6. The prosthetic hand according to claim 2, wherein at least a plurality of the bars are disposed at the inner side of the hand palm and are slidable with reference to each other and wherein distant extremities of the bars comprise a spring configured to bring the bars closer to each other.

7. The prosthetic hand according to claim 2 wherein the thumb is disposed on at least one of the bars of the construction and the construction is disposed at the back side of the hand palm.

8. The prosthetic hand according to claim 2, wherein the at least one construction comprises four constructions, each of which comprises a finger, wherein at least one of the fingers is independently movable with respect to the other fingers.

9. The prosthetic hand according to claim 8, wherein at least one of the bars comprises an intermediate swivel bar mounted to at least one of the joints at the end of the bar closest to the wrist.

* * * * *